United States Patent [19]

Idelson

[11] 4,206,115
[45] Jun. 3, 1980

[54] ORTHO-CARBOXYPHENYL AZO ORTHO-HYDROXYPYRAZOLE YELLOW DYES HAVING SILVER HALIDE DEVELOPING CAPABILITY

[75] Inventor: Elbert M. Idelson, Newton, Mass.

[73] Assignee: Polaroid Corporation, Cambridge, Mass.

[21] Appl. No.: 856,221

[22] Filed: Dec. 1, 1977

[51] Int. Cl.² .................... C09B 35/30; C09B 45/16; G03C 1/40; G03C 5/54
[52] U.S. Cl. ................... 260/163; 260/141; 260/147; 260/162; 260/570.8 R; 568/308; 450/149; 450/225; 450/390; 450/467; 450/566; 450/483; 450/222; 450/339; 450/289
[58] Field of Search ..................... 260/162, 163

[56] References Cited
U.S. PATENT DOCUMENTS

| | | | |
|---|---|---|---|
| 3,134,764 | 5/1964 | Blout et al. ................ | 260/162 |
| 3,255,001 | 6/1966 | Blout et al. ................ | 96/29 |
| 3,282,913 | 11/1966 | Green ......................... | 260/163 |
| 3,329,700 | 7/1967 | Green ......................... | 260/162 |
| 3,482,972 | 12/1969 | Idelson ....................... | 96/29 |
| 3,544,545 | 12/1970 | Idelson ....................... | 260/162 X |
| 3,551,406 | 12/1970 | Idelson ....................... | 260/162 X |
| 4,013,633 | 3/1977 | Haase et al. ................ | 260/163 X |
| 4,045,423 | 8/1977 | Brouard et al. .............. | 260/147 |

*Primary Examiner*—Floyd D. Higel
*Attorney, Agent, or Firm*—Gaetano D. Maccarone; John P. Morley

[57] ABSTRACT

Novel yellow ortho carboxy, ortho' hydroxy azo dyes having a silver halide developing capability and conforming to the formula:

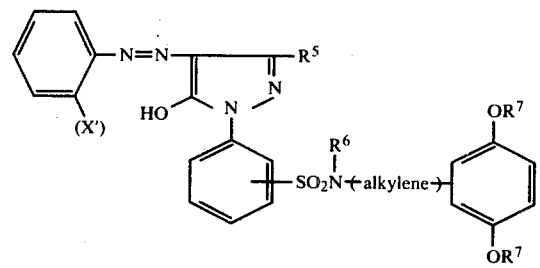

where X' is hydrogen, hydroxy, carboxy or any substituent that does not adversely affect the solubility of the compound of said formula in an aqueous alkaline photographic processing composition and does not render the oxidized form of the compound of said formula mobile in such processing composition; $R^5$ is hydrogen, hydroxyl, alkyl having from 1-6 carbon atoms or

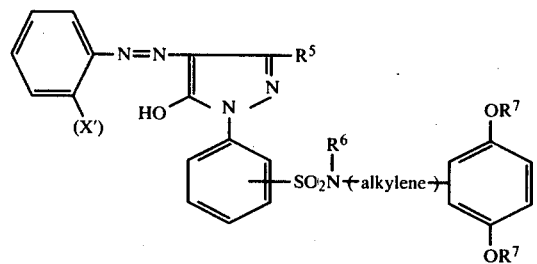

having from 1-6 carbon atoms); $R^6$ is hydrogen or alkyl; each $R^7$ is hydrogen or a protective group which can be removed to provide a dihydroxyphenyl silver halide developing substituent and -(alkylene)- has from 1-6 carbon atoms.

14 Claims, 4 Drawing Figures

ORTHO-CARBOXYPHENYL AZO ORTHO-HYDROXYPYRAZOLE YELLOW DYES HAVING SILVER HALIDE DEVELOPING CAPABILITY

BACKGROUND OF THE INVENTION

1. The Field of the Invention

This invention relates to novel yellow ortho carboxy, ortho'hydroxy azo dyes having a silver halide developing capability. The novel azo dyes of this invention are particularly useful for the preparation of yellow azo dyes having especially desirable performance characteristics in photographic products and processes.

2. Description of the Prior Art

Yellow dyes having a silver halide developing capability, e.g., a silver halide developing substituent, are known to the art. Such dyes, commonly referred to as "dye developers" are disclosed in the following U.S. Pat. Nos.: 3,134,672; 3,134,764; 3,135,604; 3,135,734; 3,141,772; 3,183,090; 3,201,384; 3,246,985; 3,252,990; 3,282,913; 3,306,891; 3,309,199 and 3,424,742.

As disclosed in these patents and, as those in the art know, dye developers essentially comprise a chromophore integrated with a silver halide developing substituent, usually a dihydroxyphenyl silver halide developing substituent. Dye developers are particularly useful in diffusion transfer photographic products and processes because of their capability in their nonoxidized form of being dissolved in aqueous alkaline photographic processing compositions and their capability of being oxidized in the presence of developed silver to provide an immobile or precipitated dye developer. This differential in mobility (or solubility) between the oxidized and nonoxidized form of a dye developer provides a diffusible pattern of nonoxidized dye developer during development of a photoexposed silver halide emulsion and the pattern can be transferred by diffusion to an image-receiving layer for viewing.

Of the yellow azo dye developers disclosed in the above patents, those considered to be most closely related to the novel yellow azo dyes of this invention are described in Column 3 of U.S. Pat. No. 3,141,772 by way of the following structure:

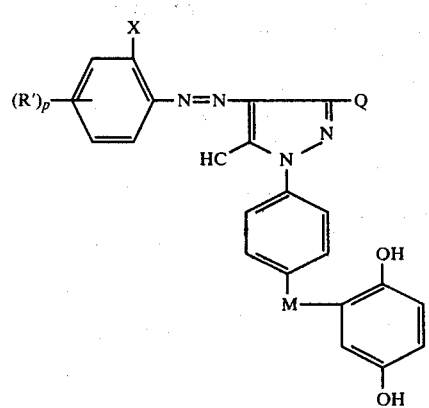

where X is hydrogen or a lower alkyl, lower alkoxy, sulfonamido, or trifluoromethyl radical and X is positioned ortho to the —N=N— group; R' is a lower alkoxy, halogen, lower alkyl, trifluoromethyl or sulfonamido radical; p is the integer 0–4 and Q is a

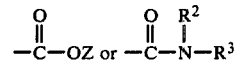

where Z is a lower alkyl radical and each $R^2$ and $R^3$ is hydrogen or an alkyl radical or $R^2$ and $R^3$ together may be a divalent aliphatic radical and M is a lower alkylene radical.

SUMMARY OF THE INVENTION

The novel yellow azo dyes of this invention can broadly be defined by the following formula:

Formula 2

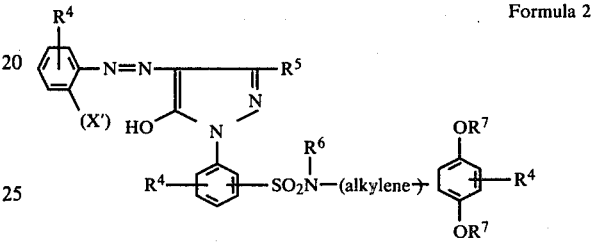

where $R^4$ can represent any substituent that will not impair the yellow absorption characteristics of the azo dye or impair the dye developer functionality of the azo dye and it should be understood that the compounds defined in the claims include such substituents even though "$R^4$" is not used in the claims to designate such substituents; X' is preferably hydrogen, hydroxy or carboxy and most preferably carboxy, but X' may be any substituent that does not adversely affect the solubility of the compound of Formula 2 in an aqueous photographic processing composition and does not render the oxidation product of the compound of Formula 2 mobile in such processing compositions; $R^5$ is hydrogen, hydroxy, alkyl having 1–6 carbon atoms or

(alkyl having 1–6 carbon atoms); $R^6$ is hydrogen or alkyl and preferably a lower alkyl having 1–4 carbon atoms; ⁻alkylene⁻ has from 0–6 carbon atoms; and each $R^7$ is hydrogen or a protective group such as acyloxy, benzyloxy, cathyloxy, alkoxy, acetoxy or like groups that can be removed such as by hydrolysis to provide the dihydroxy silver halide developing moiety with the particularly preferred $R^7$ protective groups being alkyl groups and carboalkoxy e.g., carbomethoxy and carboethoxy.

As mentioned, the particularly preferred yellow dyes of Formula 2 are those in which X' is a carboxy group and these particularly preferred compounds are of the following structure:

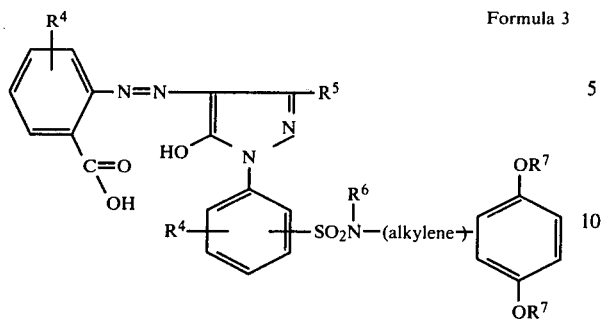

Formula 3

The novel, yellow ortho carboxy, ortho'hydroxy azo dyes of Formula 3 are particularly valuable as intermediates in the preparation of novel 2:1 chrome complexed azo dyes of the following formula:

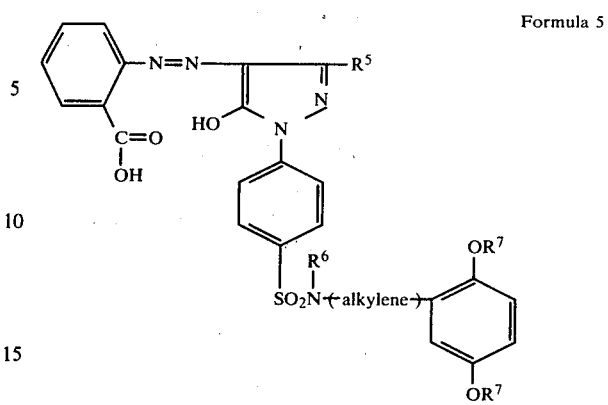

Formula 5

Particularly preferred yellow azo dyes of Formula 5

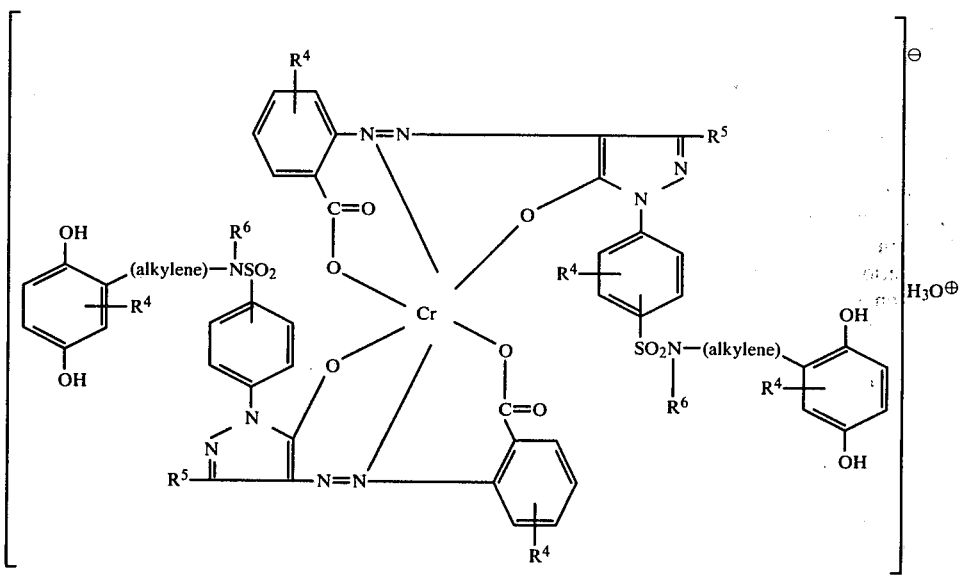

Formula 4

As will be illustrated later, yellow 2:1 chrome complexed azo dyes of Formula 4 have especially desirable performance characteristics in photographic products and processes particularly in terms of color stability.

The invention, as well as details relating to the manners of making and using it, will be more fully appreciated by the following description of the preferred embodiments taken with FIGS. 1-4.

DESCRIPTION OF THE PREFERRED EMBODIMENTS

Figure 1:
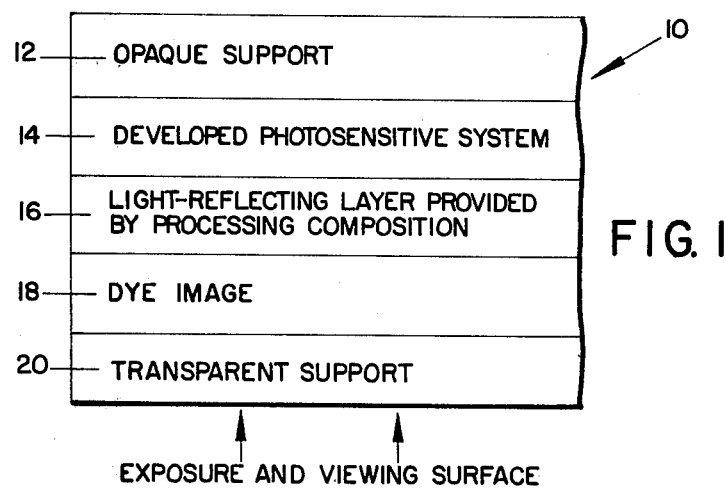
FIGS. 1-3 are simplified schematic views of arrangements of essential elements of film units having dye developers of Formula 3. The film units are shown after exposure and processing.

The preferred yellow azo dyes of Formula 2 are the ortho carboxy, ortho'hydroxy azo dyes of the formula:

are those where $R^5$ is hydrogen or lower alkyl, $R^6$ is lower alkyl and $R^7$ is hydrogen, $—CH_3$, $—CO_2CH_3$ or $—CO_2C_2H_5$.

The preferred compounds of Formula 5, as well as any of the compounds of Formula 2, may be prepared by a series of steps which initially involve the diazotization an aromatic amine and the coupling of the diazotized amine with a sulfonyl-pyrazolinone, preferably a p-sulfonyl pyrazolinone. This diazotization and coupling can be illustrated by the following reaction scheme:

Diazotization Step

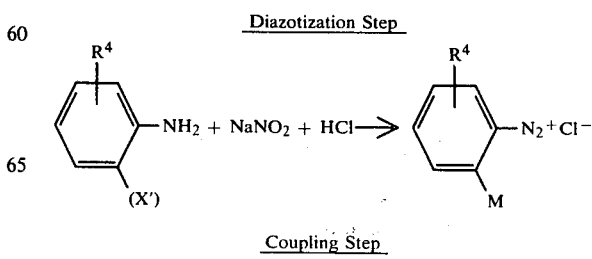

Coupling Step

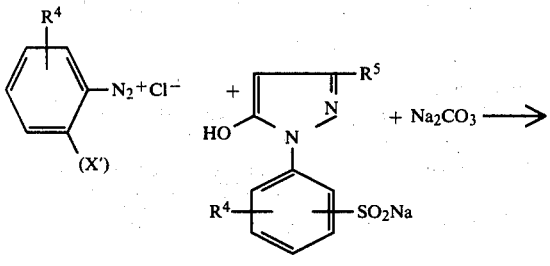

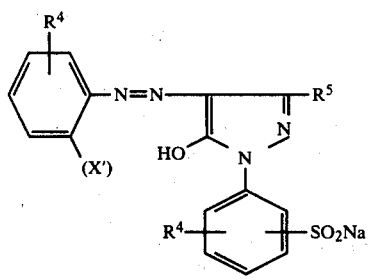

The product of the coupling step (Formula 6) is then reacted with a suitable halogenating agent to provide a compound of the following structure:

Formula 7

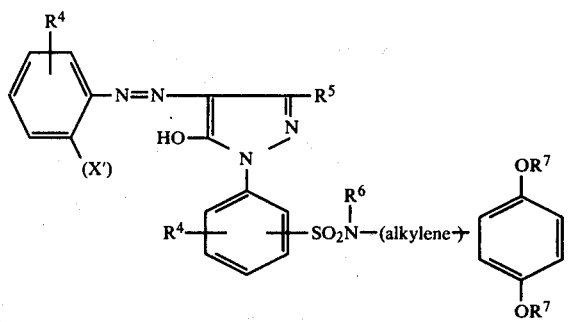

Reaction of a compound of Formula 7 with an appropriate amine will provide a yellow azo dye of Formula 2 having a silver halide developing substituent or a protected silver halide developing substituent. This reaction is illustrated by the following reaction scheme:

Formula 2

Formula 6

As mentioned, the particularly preferred yellow azo dyes of Formula 2 are those where X' is —CO$_2$CH$_3$ but it should be understood that Formula 2 includes yellow azo dyes where X' may be hydrogen, hydroxyl or other substituents such as alkyl, alkoxy, halogen, sulfonamido, amino, amido, nitro and the like.

Yellow azo dyes of Formula 2 include those where each R$^7$ is hydrogen as well as those where each R$^7$ is a protective group removable such as by hydrolysis to provide the dihydroxyphenyl silver halide developing substituent. The preferred preparations of 2:1 metal complexes of the yellow azo dye of Formula 2 involves the use of the dihydroxyphenyl substituent containing yellow azo dyes of Formula 2. However, yellow azo dyes of Formula 2 having protective groups can be used to prepare the 2:1 metal complexes with the protective groups being removed after complexing to provide the dihydroxyphenyl silver halide developing substituent.

Examples 1–4 which follow illustrate a preparation of a yellow azo dye developer of this invention.

EXAMPLE 1

This example illustrates a preparation of a preferred ortho carboxy, ortho'hydroxy azo dye of Formula 2. The illustrative preparation involves the following reaction scheme:

Step 1.
(Diazotization Step)

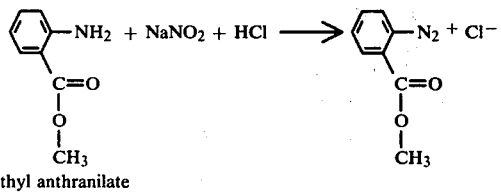

methyl anthranilate

Step 2.
(Coupling step)

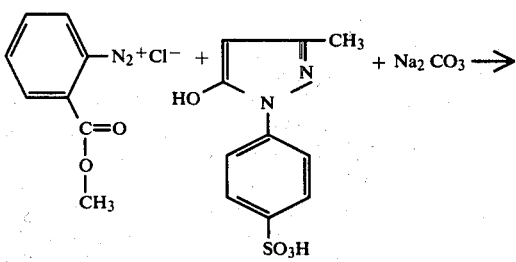

3-methyl-1-(p-sulfophenyl)2-pyrazolin-5-one.

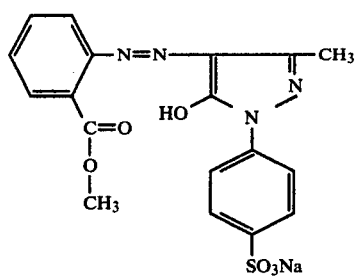

Step 1
(Diazotization Step)

30.2 gms. of methyl anthranilate (0.2 M) were suspended in 150 mls. H₂O and 50 mls. concentrated HCL (0.6 M) were added to the suspension. The mixture was then chilled to 0°–5° C. and 13.8 gms. of sodium nitrite (0.2 M) in 5 mls. H₂O were added dropwise with stirring. Stirring of the solution was continued at 5°–10° C. for about 10–15 minutes.

Step 2
(Coupling Step)

50.8 gms. of 3 methyl-1-(p-sulfophenyl)2-pyrazolin-5-one (0.2 M) were dissolved in 25 mls. H₂O and 200 mls. isopropyl alcohol together with 42.4 gms. Na₂CO₃ (0.4 M). An ice bath was used to cool the solution to about 10° C. The solution of Step 1 was then added with stirring and a yellow precipitate formed. The mixture was stirred overnight at room temperature. 500 mls. of isopropyl alcohol was added and the mixture was heated on a steam bath until the yellow precipitate was dissolved. The solution was allowed to cool slowly to room temperature. The yellow needles formed on cooling were washed with 200 mls. isopropyl alcohol and air dried. Yield of solid product was 88 gms. (95% theoretical).

The product of Step 2 was then reacted with thionyl chloride to provide the following product:

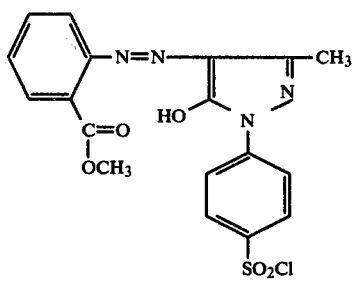

The reaction was conducted as follows:

43.5 gms. (0.1 M) of the product of Step 2 were suspended in 400 mls. of N,N-dimethylformamide and while the mixture was stirred, 50 gms. of thionyl chloride (0.46 M) were added dropwise so as to keep the reaction temperature below 40° C. No cooling was used and the temperature was controlled by the thionyl chloride addition rate. After addition of thionyl chloride, the reaction mixture was stirred overnight at room temperature. A bright yellow solid was precipitated by stirring the reactive mixture in 1 liter of chipped ice. The precipitate was filtered, washed with 250 mls. of hexane and air dried overnight. Yield of yellow product was 35 gms. (80% theoretical) m.p. 227°–229° C.

EXAMPLE 2

This example illustrates a preparation of a protected silver halide developing substituent which is reacted with the product of Example 1 to provide an ortho carboxy, ortho'hydroxy azo dye intermediate having a protected silver halide developing capability. The illustrative preparation involves the following reaction scheme:

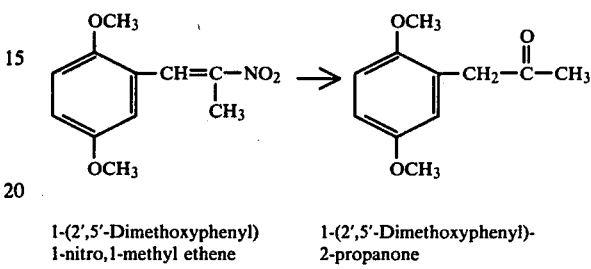

1-(2′,5′-Dimethoxyphenyl) 1-nitro,1-methyl ethene     1-(2′,5′-Dimethoxyphenyl)-2-propanone

STEP 1

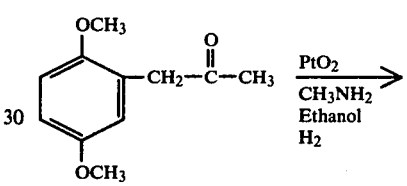

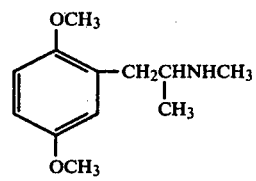

1-(2′,5′-Dimethoxyphenyl)-2-(N-methylamino) propane

STEP 2

Step 1

The following ingredients were added to a 12 liter, 3-neck flask fitted with heating mantle and stirrer:

| | | |
|---|---|---|
| 1000 gms. | - | 2-(2′,5′-Dimethoxyphenyl) 1,nitro,1-methyl ethene |
| 1340 gms. | - | iron filings (29 mesh) degreased |
| 2680 mls. | - | H₂O |
| 1000 mls. | - | benzene |
| 18 gms. | - | FeCl₃ |

The mixture was stirred, brought to reflux and 1300 mls. conc. HCl were added dropwise over about one hour. After the addition of HCl, the mixture was refluxed for about 12 hours, then cooled to room temperature and filtered through a Celite pad. The filter pad was slurried with benzene and filtered again. The filtrates were combined and the organic layer was separated, dried over MgSO₄, filtered, and the benzene removed by rotary evaporation. The product, a tan liquid, distilled at 140° C. at 1.5–2 mm. Yield of product was 604 gms. (69.6% theoretical).

Step 2

A 2 liter stirred autoclave was cooled and 2.1 gms. PtO$_2$ and 350 gms. 1-(2',5'-dimethoxyphenyl)-2-propanone were added. A cooled solution of 111 gms. monomethyl amine in 560 mls. ethanol was added and the autoclave was then charged with hydrogen (129 psi). Hydrogen uptake was rapid over the first two hours and the autoclave was stirred overnight. The product was then discharged from the autoclave, catalyst filtered from the product and the solvents were rotary evaporated. The 1-(2',5'-dimethoxyphenyl)-2-(N-methyl amino) propane distilled at about 130° C. at 0.5 mm.

EXAMPLE 3

This example illustrates a preparation of an ortho carboxy, ortho' hydroxy azo dye developer intermediate by reacting the products of Examples 1 and 2. The illustrative preparation involves the following reaction scheme:

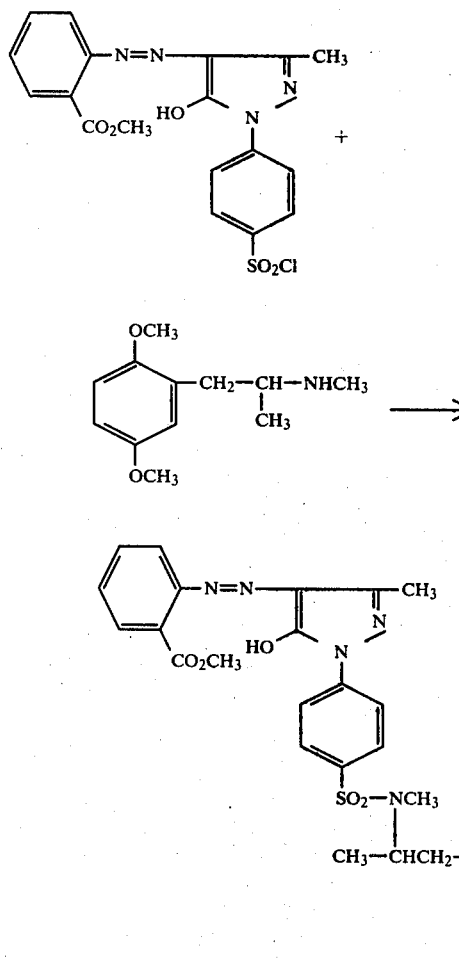

The azo dye of Example 1 (21.6 g.; 0.05 mole), the blocked developer of Example 2 (14.5 g.; 0.05 mole) and triethylamine (5.0 g.; 0.05 mole) were combined with toluene (500 ml.) in a one liter round-bottom glask equipped with N$_2$-inlet, thermometer, mechanical stirrer, condenser, drying tube, and heating mantle. The reaction was heated for 2 hours at 80°-85° C., after which time the thin layer chromatography (TLC) (Silica, CHCl$_3$) no longer showed any starting material. The reaction was then cooled to room temperature, the triethylamine hydrochloride was filtered out and the filtrate was rotary evaporated to an orange oil which solidified in a glassy form. The product was recrystallized from 2 l. ethanol 2 B. Yield: 21.5 g.; 71%.

Properties of Compound:
MOL.WT.: 607.69; MOL. FORMULA: N$_5$O$_7$SC$_{30}$H$_{33}$
m.p.: 149°-56° b.p.: Color and State: Yellow Solid
Soly.: toluene, CH$_2$Cl$_2$, CHCl$_3$
UV,Visible: PANo. 20393λ max=395
Solvent: CHCl$_3$; ε=27,600

| | C | H | N | S |
|---|---|---|---|---|
| Elemental Analysis: Found: | 59.93 | 5.54 | 11.97 | 5.45 |
| Theory: | 59.30 | 5.47 | 11.52 | 5.28 |

EXAMPLE 4

This example illustrates a preparation in which both the 2',5'-dimethoxy groups substituted on the phenyl radical and the methyl ester of the compound of the above example are converted to hydroxy substituents. The illustrative preparation involves the following reaction scheme:

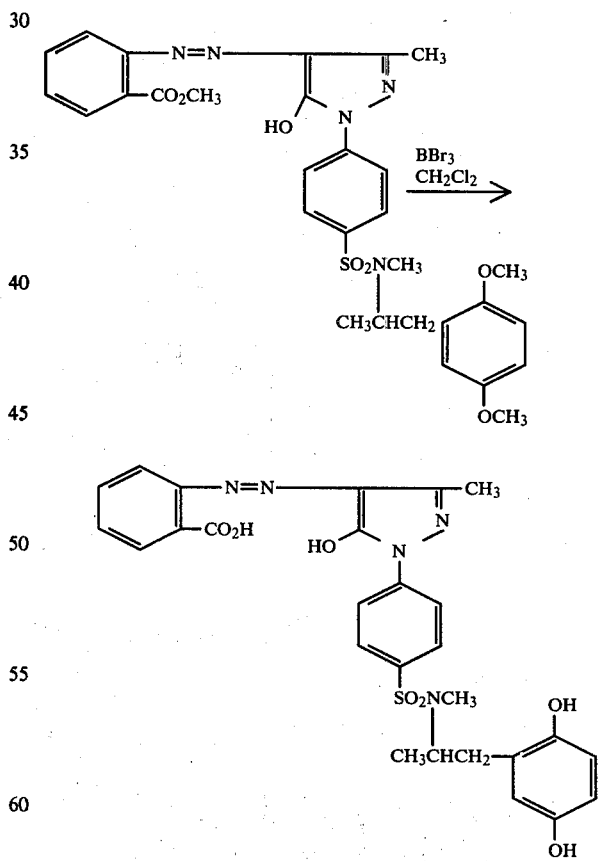

Boron tribromide 20 g. (d=2.64 g/ml.; 0.08 mole) was dissolved in CH$_2$Cl$_2$ (50 ml.) in a previously flamed system consisting of a 3-neck 1-liter round-bottom flask equipped with dropping funnel (250 ml.), N$_2$-inlet, mechanical stirrer, condenser, and drying tube. The reaction flask was surrounded by a cold water bath (10°–15° C.). The dye (Example 3; 6.0 g.; 0.01 mole) was dissolved in 180 ml. CH$_2$Cl$_2$ and added to the stirred reaction mixture over 1 hour via the dropping funnel. Solid precipitated during the addition. The reaction mixture was stirred for 1½ hours after the addition was complete and the water bath was allowed to warm gradually to r.t. when it was replaced with another ice bath. 150 ml. ethyl ether were added via the dropping funnel, with the first few ml. added very cautiously. When addition was complete, the ice bath was exchanged for a hot water bath and ether and CH$_2$Cl$_2$ were distilled off. 300 ml. hot water were added to the orange residue in the flask and stirred vigorously for 15 minutes. The orange solid was filtered out and washed with water and recrystallized from 300 ml. methoxy ethanol.

Properties of the Compound
 MOL.WT.: 565.61; MOL. FORMULA: N$_5$O$_7$SC$_{27}$H$_{27}$
 m.p.: 290°–3° b.p.: Color and State: yellow Solid
 Soly.: 2% in hot methyl cellosolve
 UV,Visible: PANo. 20394λ max=397
 Solvent: methyl cellosolve ε=26,000

| | C | H | N | S |
|---|---|---|---|---|
| Elemental Analysis: Found: | 56.96 | 4.98 | 12.39 | 5.62 |
| Theory: | 57.34 | 4.81 | 12.38 | 5.67 |

The following example illustrates the use of the product of Example 4 in preparing a 2:1 chrome complexed yellow ortho carboxy, ortho' hydroxy azo dye developer.

EXAMPLE 5

This example illustrates a preparation of the 2:1 chrome-complexed yellow dye developer of Formula 3. The illustrative preparation involves the following reaction scheme:

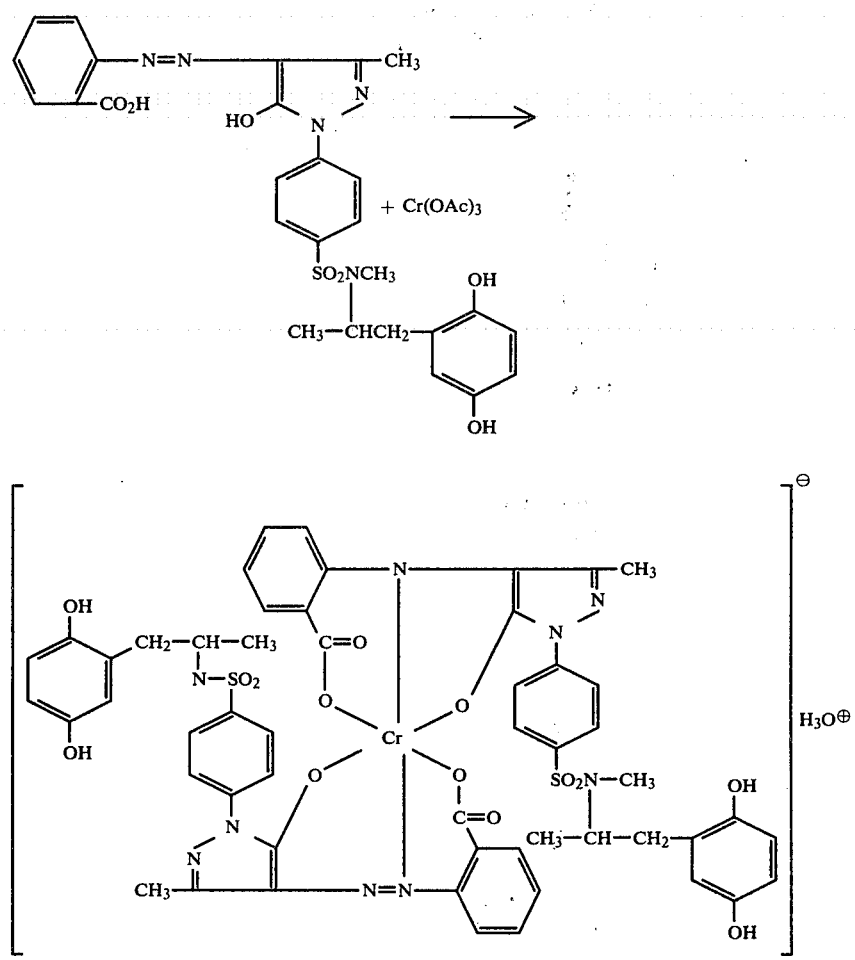

The dye developer (Example 4, 20 g.; 35.4 m mole), chromium acetate (8.75 g.; 35.4 m mole), triethylamine (3.6 g.; 35.6 m mole), and DMF (dimethyl formamide) (200 ml.) were combined in a 3-neck 500 ml. round-bottom flask equipped with N$_2$-inlet, thermometer condenser, magnetic stirrer and heating mantle. The mixture was stirred under a gentle flow of nitrogen and heated at 100°–110° C. for one hour.[1] The cooled reaction mixture was poured into 2 l water containing a little concentrated HCl. A brown solid was filtered out, washed generously with water and air dried.

(1) Reaction may be followed by TLC (silicaa, 10% MeOH/CHCl$_3$).

The crude solid was dissolved in 100 ml. DMF at room temperature. The filtered solution was precipitated into 1 liter filtered water containing a little concentrated HCl. A brown solid was filtered out, washed with water and air dried.

This solid was precipitated twice more in a sililar manner using methanol (300 ml. and 150 ml.) and filtered water (3 l and 1.5 l) containing a little concentrated HCl.

The material which is not soluble in the first methanol solution should not be discarded. If it is precipitated again using DMF (~30 ml.) and filtered water (300 ml.) containing a little concentrated HCl, pure material will be obtained.

Properties of the Compound:
MOL.WT.: 1198.21 MOL. FORMULATION: $N_{10}O_{14}S_2C_{54}H_{50}$; $Cr;H_3O+$
 Color and State: Brown Solid
 Soly.: methanol, DMF
 UV,Visible: PANo. 20409$\lambda$max—430
 Solvent: methyl cellosolve$\epsilon$=26,000

|  |  | C | H | N | S | Cr |
|---|---|---|---|---|---|---|
| Elemental Analysis: | Found: | 54.25 | 4.33 | 11.74 | 5.21 | 4.38 |
|  | Theory: | 54.13 | 4.46 | 11.69 | 5.35 | 4.34 |

The 2:1 chrome complexed yellow ortho carboxy, ortho' dydroxy azo dyes of Formula 3 are particularly useful in diffusion transfer photographic products and processes. The 2:1 chrome complexed dye of Example 5 has found to be particularly advantageous when used in integral negative positive film units of the type described in U.S. Pat. Nos. 3,415,644 and 3,647,437.

A representative film unit of this type is shown as 10 in FIG. 1 and includes a light reflecting layer provided by a light-reflecting pigment in a processing composition initially present in a rupturable processing container (not shown) and distributed after photoexposure of photosensitive layer(s) 14 through transparent support 20 and image-receiving layer 18. Processing compositions used in such film units are aqueous alkaline photographic processing compositions comprising an opacifying system which include a titanium dioxide pigment as the light-reflecting agent, preferably in combination with an optical filter agent described in detail in U.S. Pat. No. 3,647,437. When the processing composition is distributed over all portions of photo-exposed photosensitive system 14, a light-reflecting layer 16 comprising the titanium dioxide is provided between image-receiving layer 18 and photosensitive layer 14. Application of the processing composition initiates development of photo-exposed photosensitive layer(s) 14 in manners well known to the art to establish an imagewise distribution of diffusible image-providing material which can comprise silver but preferably comprises one or more dye image-providing material. The diffusible image-providing material(s) is transferred through permeable, light-reflecting titanium dioxide-containing layer 16 where it is mordanted, precipitated or otherwise retained in known manner in image-receiving layer 18. The transfer image is viewed through transparent support 20 against light-reflecting layer 16.

Figure 2:
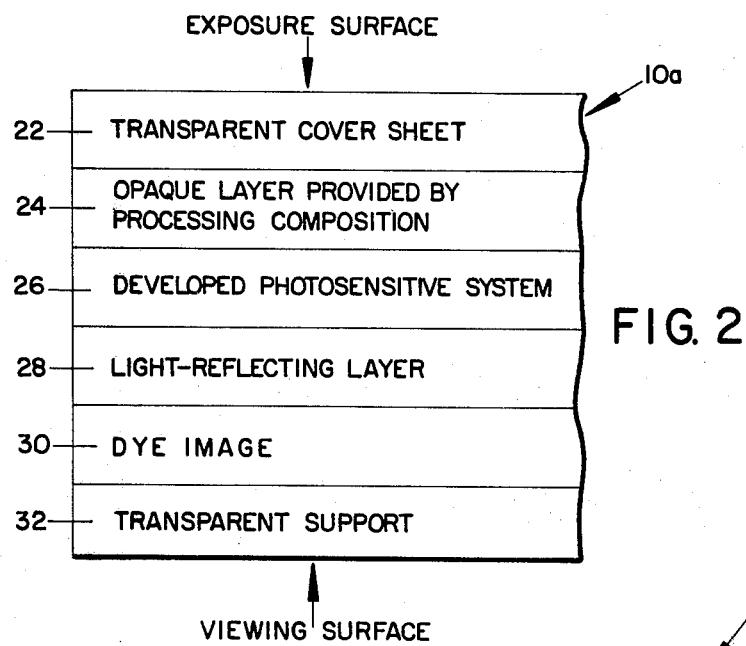

FIG. 2 shows an arrangement of essential elements of an integral negative-positive film unit of the type described in U.S. Pat. No. 3,594,165 and British Pat. No. 1,330,524 following exposure and processing. The film unit 10a includes a processing composition initially retained in a rupturable container (not shown) and distributed between cover sheet 22 and photosensitive system or layer 26 after photoexposure of photosensitive element(s) 26 through transparent cover sheet 22. Processing compositions used in such film units are aqueous alkaline photographic processing compositions which include an opacifying system comprising an opaque pigment which need not be—and usually is not—light reflecting. After distribution of the processing composition between transparent cover sheet 22 and photoexposed photosensitive layer 26, an opaque layer 24 is installed which protects layer 26 from further photoexposure through cover sheet 22. Like the film units of FIG. 1, as and after opaque layer 24 is installed, the processing composition initiates development of photoexposed photosensitive layer 26 to establish an imagewise distribution of the image-providing materials in manners well known to the art. For example, the processing composition alone my cause development or developing agents may be in the processing composition initially and/or the agents may be in the film unit so that they may be carried to layer 26 by the processing composition. The imagewise distribution is transferred through permeable light-reflecting pigment containing layer 28 to dye image element 30 for viewing through transparent support 32 against the light-reflecting pigment containing layer 28. Oftentimes an opaque layer (not shown) is positioned between reflecting layer 28 and photosensitive layer 26.

Figure 3:
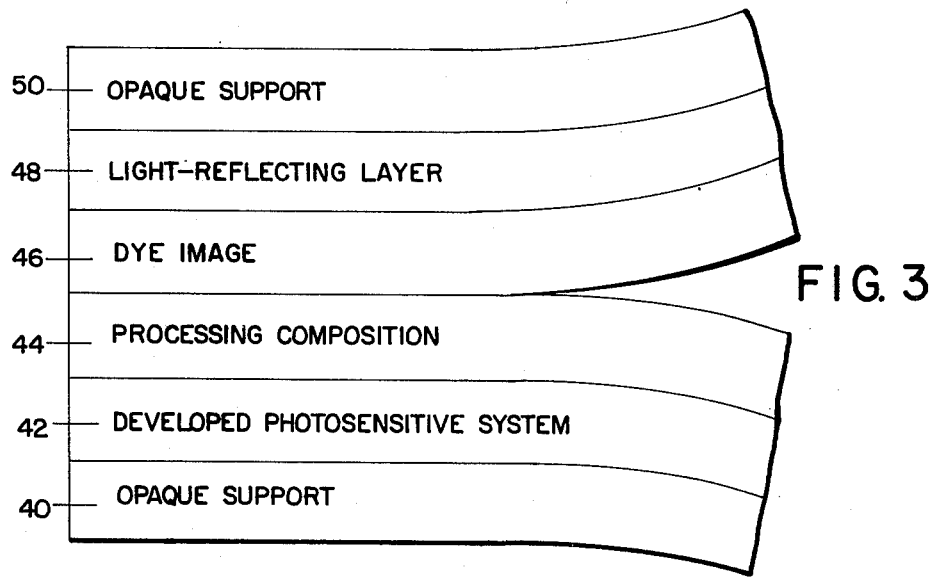

The novel dye developers of the present invention also may be utilized in film units designed to be separated after processing such as those described in U.S. Pat. No. 2,943,606. Such a diffusion transfer film unit of the present invention is shown in FIG. 3 as 10b. The film unit shown there comprises a photosensitive element having an opaque support 40 carrying a photosensitive system containing layer(s) 42. In film units of this type the photosensitive element is photoexposed and processing composition 44 is then distributed over the photoexposed system. During processing an image-receiving element comprising dye image layer 46 carried by support 50—preferably opaque—is superposed on photoexposed photosensitive element. Like the film units of FIGS. 1 and 2, the processing composition permeates layer(s) 42 to provide an imagewise distribution of diffusible dye image-providing materials which is transferred to dye image layer 46. Unlike the film units of FIGS. 1 and 2, however, the transferred dye image is viewed in layer 46 against light-reflecting background layer 48 after separation of the image-receiving element from the photosensitive element.

Example 6 which follows presents a comparison of the performance characteristics of a particularly preferred 2:1 chrome-complexed yellow dye developer of this invention (the 2:1 chrome-complexed yellow dye developer of Example 5) and a 1:1 chrome-complexed yellow dye developer extensively used in commercial film units; the 1:1 chrome-complexed yellow dye developer of the following formula:

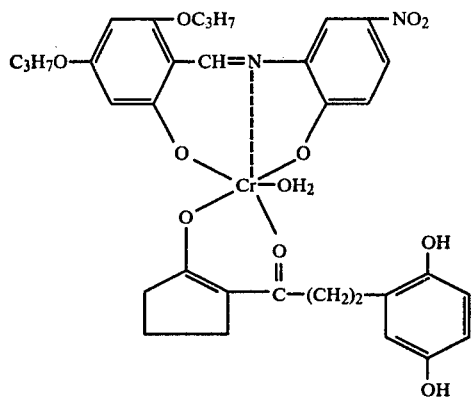

The comparison involved diffusion transfer film units having multicolor photosensitive elements which contained the following cyan and magenta dyes developers:

cyan:

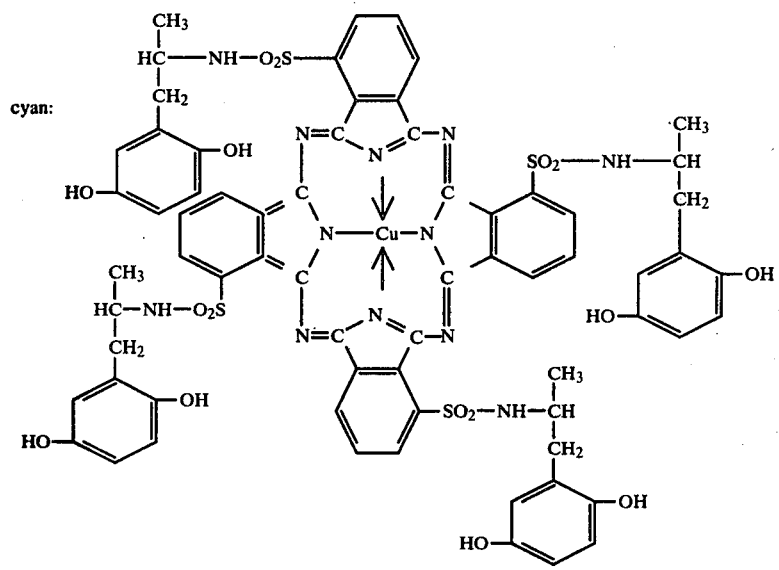

magenta:

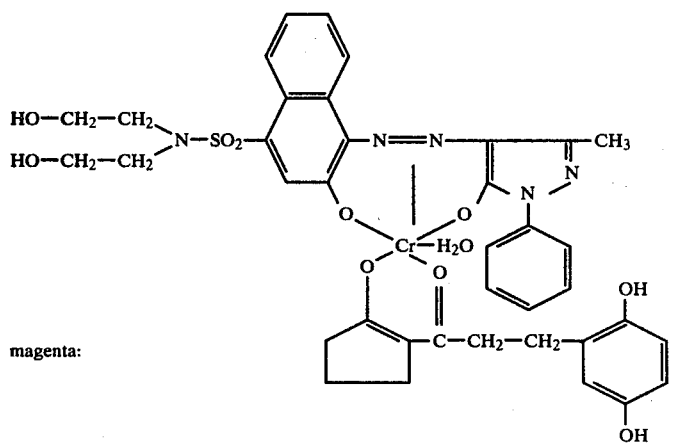

Also, except for variations in the yellow dye developer layer which are explained in Example 6, the photosensitive elements of the film units of Example 6 were prepared by coating a gelatin-subcoated, 4 mil., opaque polyethylene terephthalate film base with the following layers:

1. A layer of cyan dye developer and 2-phenyl benzimidazole (antifoggant) dispersed in gelatin and coated at a coverage of about 55 mgs./ft.$^2$ dye, about 22 mgs./ft.$^2$ of 2-phenyl benzimidazole, 112 mgs./ft.$^2$ of gelatin;

2. A red-sensitive gelatino silver iodobromide emulsion coated at a coverage of about 80 mgs./ft.$^2$ of silver and about 104 mgs./ft$^2$ of gelatin;

3. A layer of a 60-30-4-6 tetrapolymer of butylacrylate, diacetone acrylamide, styrene and methacrylic acid and polyacrylamide coated at a coverage of about 428 mgs./ft.$^2$ of the copolymer and about 23 mgs./ft.$^2$ of polyacrylamide;

4. A layer of magenta dye developer and 2-phenyl benzimidazole dispersed in gelatin and coated at a coverage of about 60 mgs./ft.$^2$ of dye about 21 mgs./ft.$^2$ of 2-phenyl benzimidazole and about 40 mgs./ft.$^2$ of gelatin;

5. A green-sensitive gelatino silver iodobromide emulsion coated at a coverage of about 60 mgs./ft.$^2$ of silver and about 43 mgs./ft.$^2$ of gelatin;

6. A layer containing the tetrapolymer referred to above in layer 3 and polyacrylamide coated at a coverage of about 230 mgs./ft.² of copolymer and about 20 mgs./ft.² of polyacrylamide;

7. A layer of yellow dye developer and 2-phenyl benzimidazole dispersed in gelatin and coated at the coverages specified in Example 6.

8. A blue-sensitive gelatino silver iodobromide emulsion layer coated at a coverage of about 110 mgs./ft.² of silver and about 52 mgs./ft.² of gelatin and 9. A layer of carbon black dispersed in gelatin coated at a coverage to provide about 4 mgs./ft.² of carbon black and about 40 mgs./ft.² of gelatin.

The image-receiving elements of the film units of Example 9 were prepared by coating transparent 4 mil polyethylene terephthalate film base with the following layers:

1. As a polymeric acid layer, the partial butyl ester of polyethylene/maleic anhydride copolymer at a coverage of about 0.2500 mgs./ft.²;

2. A timing layer containing a 40:1 ratio of a 60-30-4-6 tetrapolymer of butylacrylate, diacetone acrylamide, styrene and methacrylic acid and polyvinyl alcohol at a coverage of about 500 mgs./ft.²; and 3. A polymeric image-receiving layer containing a 2:1 mixture, by weight, of polyvinyl alcohol and poly-4-vinylpyridine, at a coverage of about 300 mgs./ft.².

The so prepared image-receiving and photosensitive elements can be taped together with opaque tape extending around the edges to provide an integral film unit. A rupturable container retaining an aqueous alkaline processing solution was mounted in a fixed position on the leading edge of each of the elements, by pressure-sensitive tapes, so that, pressure applied to the container would rupture the container's marginal seal and its contents could be distributed between the image-receiving layer and the gelatin overcoat layer of the photosensitive element.

In each of the film units of Example 6, the aqueous alkaline processing composition comprised:

| | | |
|---|---|---|
| Water | 1918 | cc |
| Potassium hydroxide (85) | 509 | g. |
| N-phenethyl-α-picolinium bromide (50% solution in water) | 110.4 | g. |
| Carboxymethyl cellulose (Hercules Type 7H4F providing a viscosity of 3,000 cps. at 1% in water at 25° C.) 95% solids | 80.3 | g. |
| Titanium dioxide | 1842 | g. |
| 6-methyl uracil | 9.3 | g. |
| bis-(β-aminoethyl)-sulfide | 1.4 | cc |
| Lithium nitrate | 4.8 | g. |
| Benzotriazole | 34.6 | g. |
| Colloidal silica aqueous dispersion (30% SiO₂) | 77.6 | g. |
| N-2-hydroxyethyl-N,N',N'-tris-carboxymethyl-ethylene diamine | 36.4 | g. |
| Polyethylene glycol (molecular weight 6,000) | 22.7 | g. |
| 4-amino pyrazolo pyrimidine | 11.3 | g. |
| (2-benzimidazoyl methyl) sulfide hydrate | 0.95 | g. |
| | 93.4 | g. |

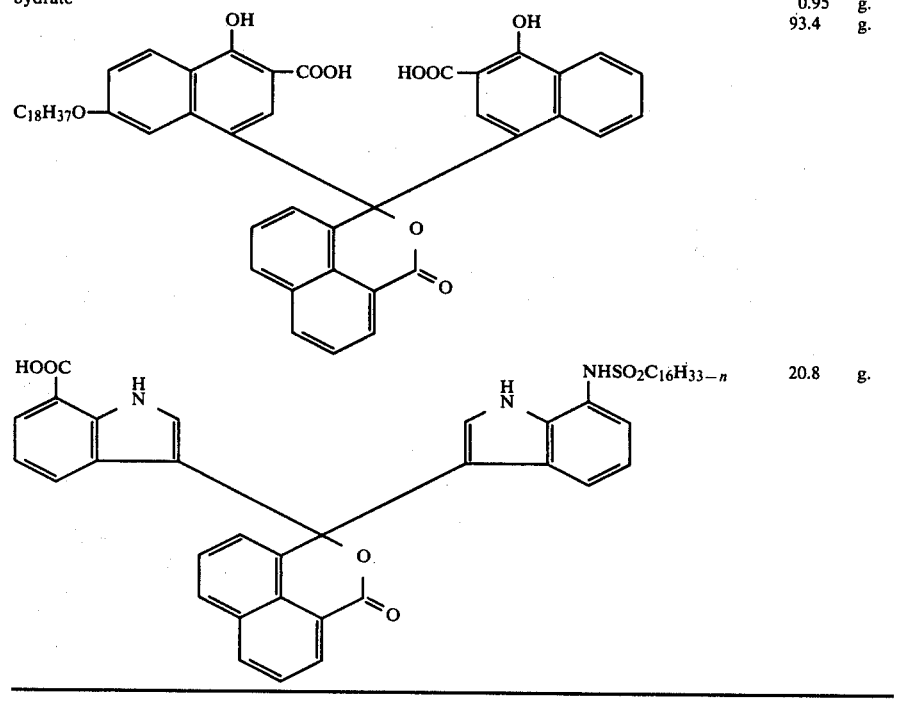

| | |
|---|---|
| | 20.8 g. |

The photosensitive element of such prepared integral film units may be exposed through the transparent support of the image-receiving element, and a layer of the processing composition may be distributed by passing the film unit between a pair of pressure-applying rolls.

EXAMPLE 6

Figure 4:
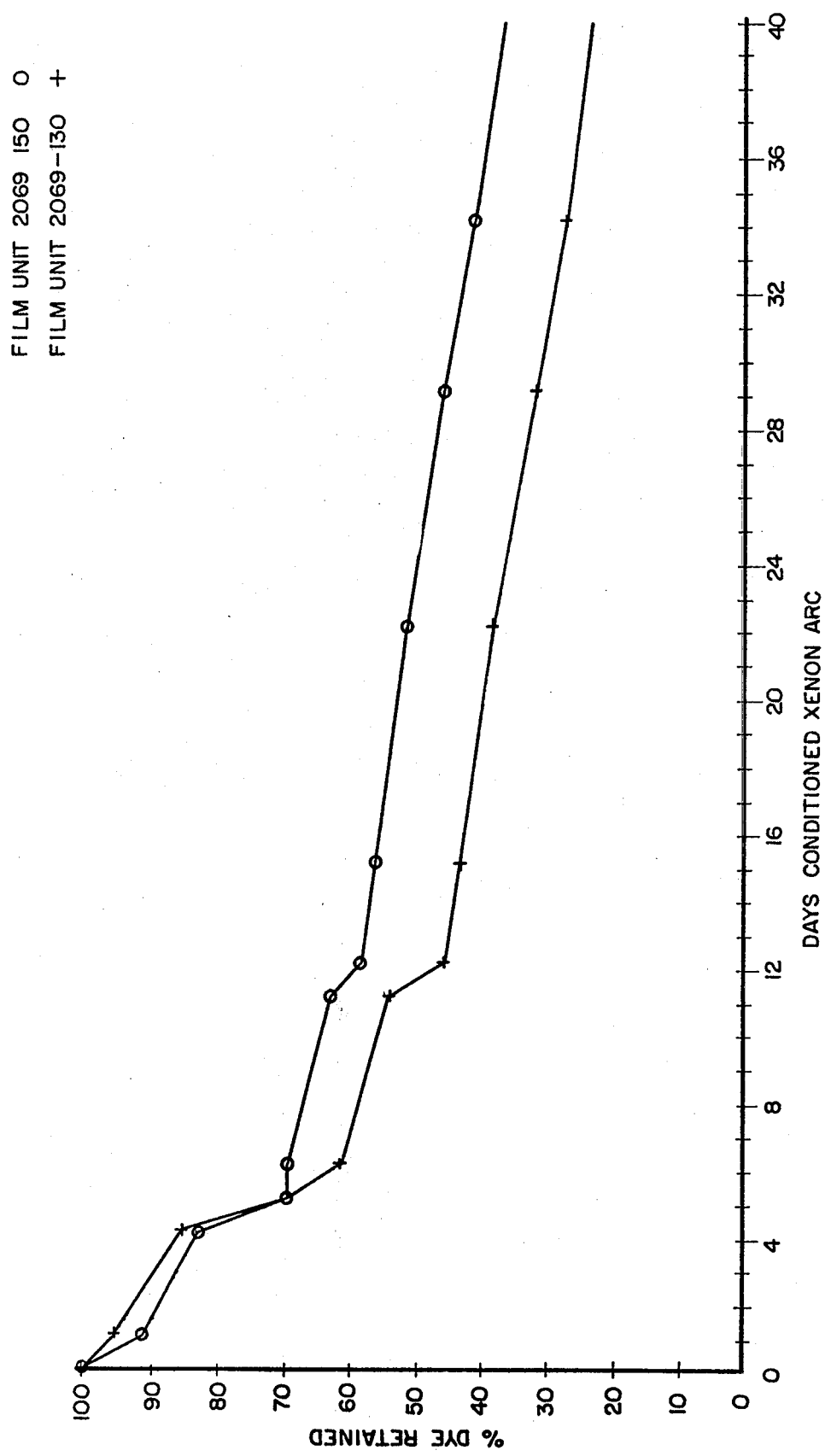
FIG. 4 graphically depicts dye stability data obtained in Example 6.

This example presents a comparison of dye stability measurements for two film units, one containing a 1:1 chrome-complexed yellow dye developer of the prior art (Formula 7) and the other containing a 2:1 chrome-complexed yellow dye developer of this invention. FIG. 4 graphically depiects the dye stability measurements.

The two film units had multicolor photosensitive elements prepared as described before and were substantially the same except for the yellow dye developer layers. In the film unit designated as 2069-150 of FIG. 4, the yellow dye containing layer contained the 2:1 chrome-complexed yellow dye developer of Example 5 and 2-phenyl benzimidazole dispersed in gelatin at a coverage of about 8.7 mgs./ft.$^2$ yellow dye developer, about 20 mgs./ft.$^2$ of 2-phenyl benzimidizole and about 18 mgs./ft.$^2$ of gelatin. In the film unit designated as 2069-130 of FIG. 4, the yellow dye developer layer contained the 1:1 chrome complexed yellow dye developer of Formula 7 and 2-phenyl benzimidazole dispersed in gelatin at a coverage of about 67 mgs./ft.$^2$ of yellow dye developer, about 18 mgs./ft.$^2$ of 2-phenyl benzimidazole and about 33 mgs./ft.$^2$ of gelatin. It will be noted that the coverages of yellow dye developer in each film unit are different (87 mgs./ft.$^2$ V. 67 bgs./ft.$^2$). This difference, however, was intended and is based on considerations involving such factors as the extinction coefficient, the molecular weight and the molecular structure of each dye developed to estimate coverages for each dye developer which can provide approximately equivalent yellow optical densities for each exposed and processed film unit.

The film units were exposed to two meter candle seconds through a yellow filter and processed by passing each film unit between a pair of pressure-applying rolls to thereby distribute a layer of processing composition about 0.0028" thick between the image-receiving layer and the gelatin/carbon black overcoat of the photosensitive element. Under such exposure conditions only yellow dye was transferred to the image-receiving layer and both processed film units had comparable yellow color densities.

The processed film units were maintained at room temperature for twenty-four hours and then the dye stability of each unit was determined by exposing each unit to the conditions of a Xenon Arc Weatherometer over a period of forty days and periodically measuring the percent yellow dye retained for each unit. During this forty-day period, the light output for the Weatherometer ranged between 7000 to 9000 foot candles. FIG. 4 graphically depicts the data obtained over the forty-day period and the data clearly evidences superior performance characteristics for the preferred 2:1 chrome-complexed yellow dye of Example 5 (Film unit 2069-150) especially in terms of the stability of dye.

From the above description, it should be apparent that the present invention presents to the art novel yellow ortho carboxy, ortho' hydroxy azo dyes particularly useful in preparing 2:1 chrome-complexed yellow azo dye developers having a desirable degree of performance characteristics in terms of color, as well as stability. Accordingly, many modifications can be made in details of the above examples offered for purposes of illustrating preferred embodiments of the invention without departing from the spirit and scope of the invention defined in the claims.

What is claimed is:

1. A compound of the formula:

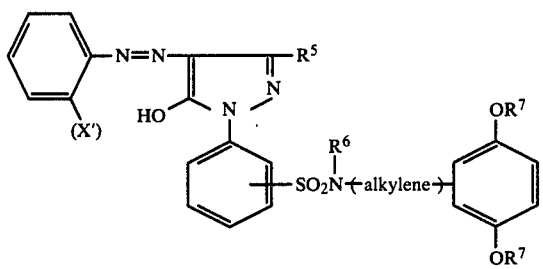

where X' is hydrogen, hydroxy, carboxy or any substituent that that does not adversely affect the solubility of the compound of said formula in an aqueous alkaline photographic processing composition and does not render the oxidized form of the compound of said formula mobile in such processing composition; R$^5$ is hydrogen, hydroxyl, alkyl having from 1-6 carbon atoms or

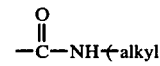

having from 1-6 carbon atoms); R$^6$ is hydrogen or alkyl; each R$^7$ is hydrogen or a protective group which can be removed to provide a dihydroxyphenyl silver halide developing substituent and-(-alkylene-)-has from 1-6 carbon atoms.

2. A compound of claim 1 where X' is

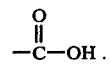

3. A compound of claim 1 where R$^5$ is alkyl.
4. A compound of claim 1 where R$^7$ is hydrogen, —CH$_3$, —CO$_2$CH$_3$ or —CO$_2$C$_2$H$_5$.
5. A compound of the formula:

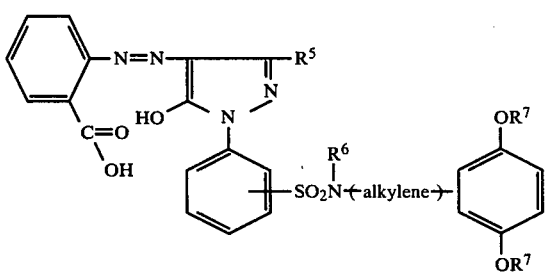

where R$^5$ is hydrogen, hydroxyl, alkyl having from 1-6 carbon atoms or

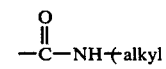

having from 1-6 carbon atoms); R$^6$ is hydrogen or alkyl; each R$^7$ is hydrogen or a protective group which can be removed to provide the dihydroxyl phenyl substituent and-(-alkylene-)-has from 0-6 carbon atoms.

6. A compound of claim 5 where $R^5$ is alkyl.

7. A compound of claim 5 wherein each $R^7$ is hydrogen, $—CH_3$, $—CO_2CH_3$ or $—CO_2C_2H_5$.

8. A compound of claim 5 wherein —alkylene— has 3 carbon atoms.

9. A compound of the formula:

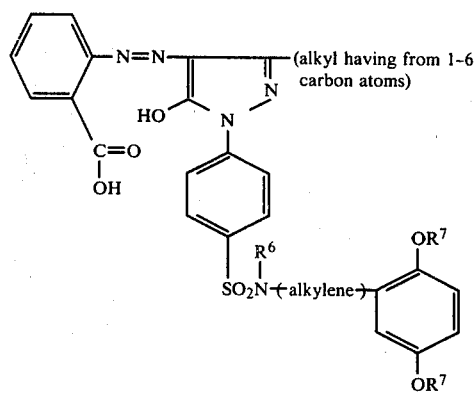

$R^6$ is hydrogen or alkyl; +alkylene+ has from 0–6 carbon atoms and each $R^7$ is hydrogen $—CH_3$, $—CO_2CH_3$ or $—CO_2C_2H_5$.

10. A compound of claim 9 where +alkylene+ has 3 carbon atoms.

11. A compound of claim 9 of the formula

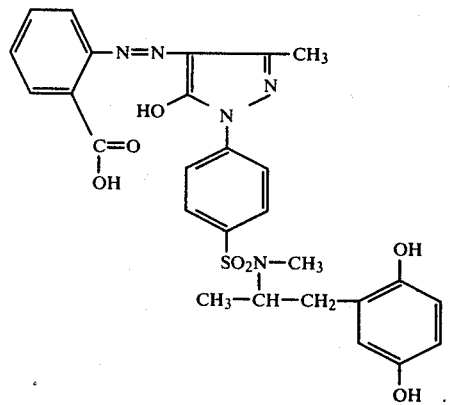

12. A compound of claim 9 of the formula

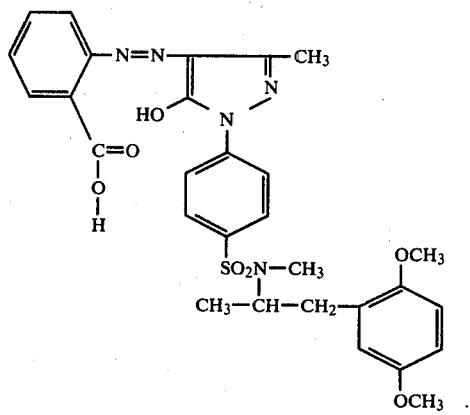

13. A compound of claim 9 of the formula

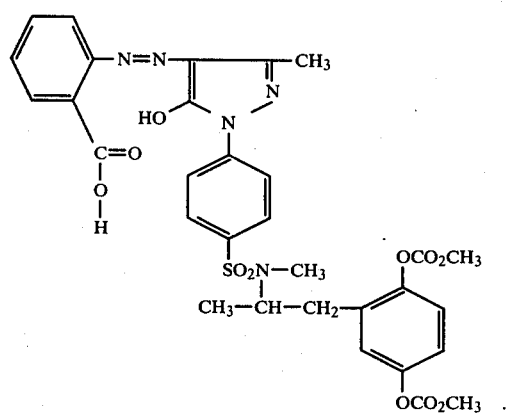

14. A compound of claim 9 of the formula:

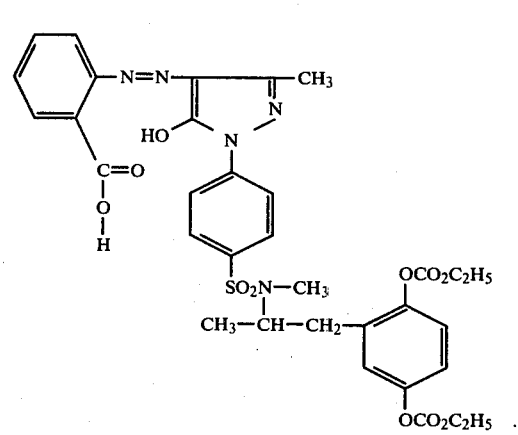

* * * * *